United States Patent

Suzuki

[11] Patent Number: 6,068,603
[45] Date of Patent: May 30, 2000

[54] MEDICAL INSTRUMENT FOR USE IN COMBINATION WITH AN ENDOSCOPE

[75] Inventor: Takayuki Suzuki, Hachioji, Japan

[73] Assignee: Olympus Optical Co., Ltd., Tokyo, Japan

[21] Appl. No.: 09/232,533

[22] Filed: Jan. 18, 1999

[30] Foreign Application Priority Data

Feb. 17, 1998 [JP] Japan .................................. 10-034785

[51] Int. Cl.⁷ .................................................. A61B 10/00
[52] U.S. Cl. .......................... 600/565; 600/564; 606/46; 606/113; 606/114; 606/170
[58] Field of Search .................... 600/562, 564, 600/565, 566, 567, 104, 153, 156, 158; 606/45, 46, 113, 114, 115, 167, 170; 604/264, 280, 22

[56] References Cited

U.S. PATENT DOCUMENTS

| | | | |
|---|---|---|---|
| 3,835,842 | 9/1974 | Iglesias | 606/46 |
| 5,133,360 | 7/1992 | Spears | 600/567 |
| 5,376,094 | 12/1994 | Kline | 606/113 |
| 5,573,008 | 11/1996 | Robinson et al. | 600/567 |
| 5,741,271 | 4/1998 | Nakao et al. | 606/114 |
| 5,810,764 | 9/1998 | Eggers et al. | 604/114 |
| 5,846,248 | 12/1998 | Chu et al. | 606/113 |
| 5,897,487 | 4/1999 | Ouchi | 600/127 |
| 5,961,526 | 10/1999 | Chu et al. | 606/113 |
| 5,976,073 | 11/1999 | Ouchi | 606/113 |
| 5,976,129 | 11/1999 | Desai | 606/40 |

FOREIGN PATENT DOCUMENTS

| | | |
|---|---|---|
| 0 761 170 A2 | 3/1997 | European Pat. Off. . |
| 10-146345 | 6/1998 | Japan . |
| WO 95/08291 | 3/1995 | WIPO . |

*Primary Examiner*—Cary O'Connor
*Assistant Examiner*—Charles Marmor, IV
*Attorney, Agent, or Firm*—Frishauf, Holtz, Goodman, Langer & Chick, P.C.

[57] ABSTRACT

A flat section is provided at a distal end of a snare pipe located in a sheath. When a snare is pushed, the snare is moved in the snare pipe with a looped expansible section of the snare kept in contact with both opposite sides of the flat section. As a result, the expansion direction of the looped section is regulated.

22 Claims, 10 Drawing Sheets

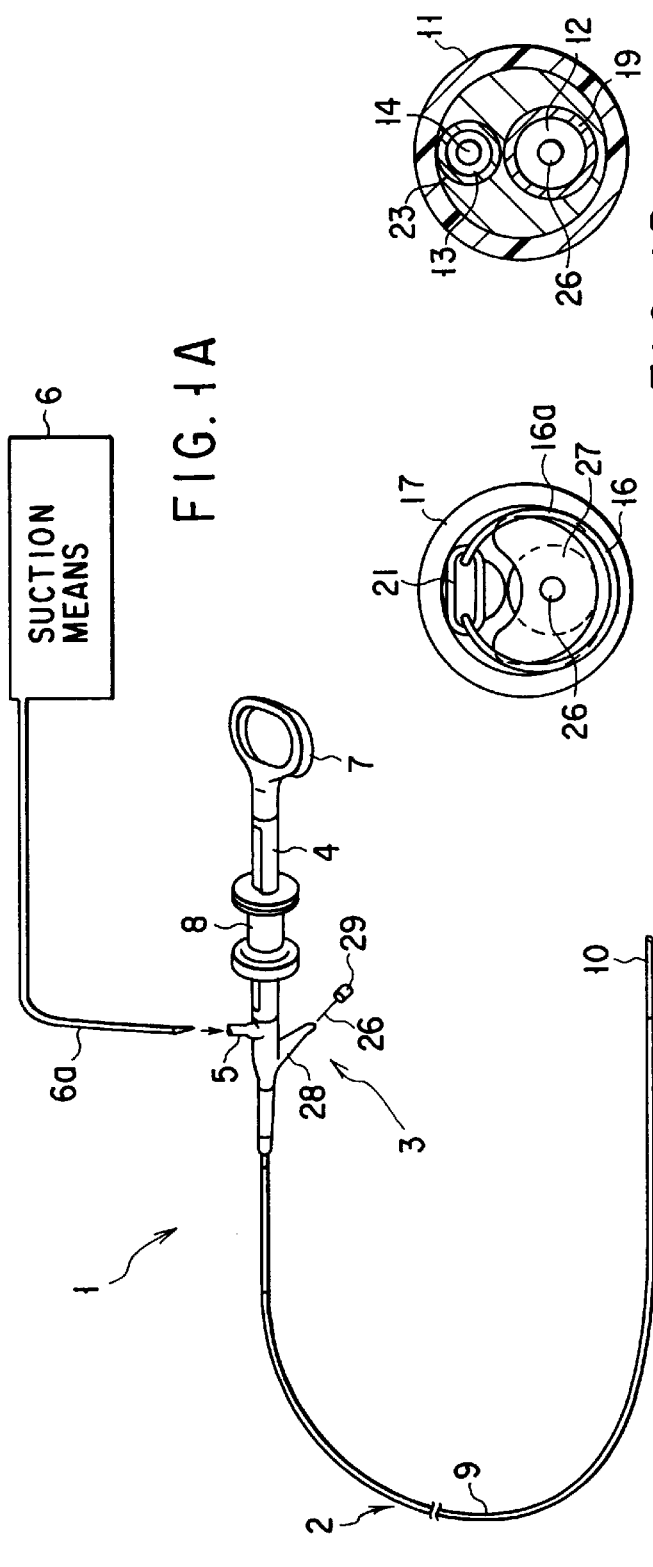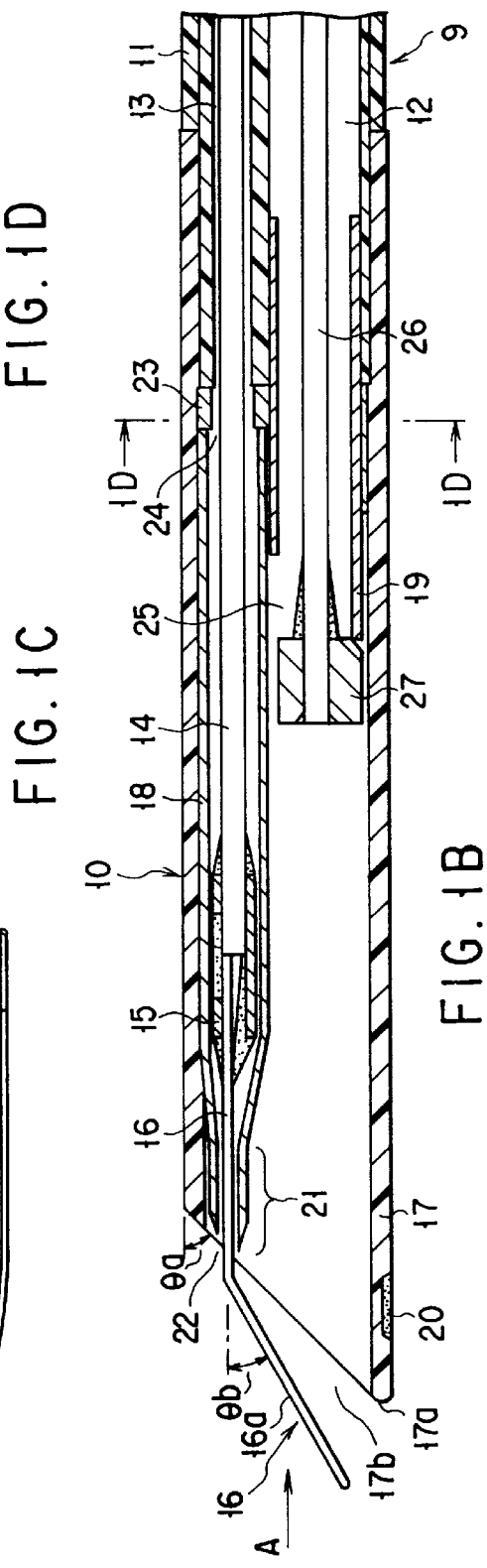

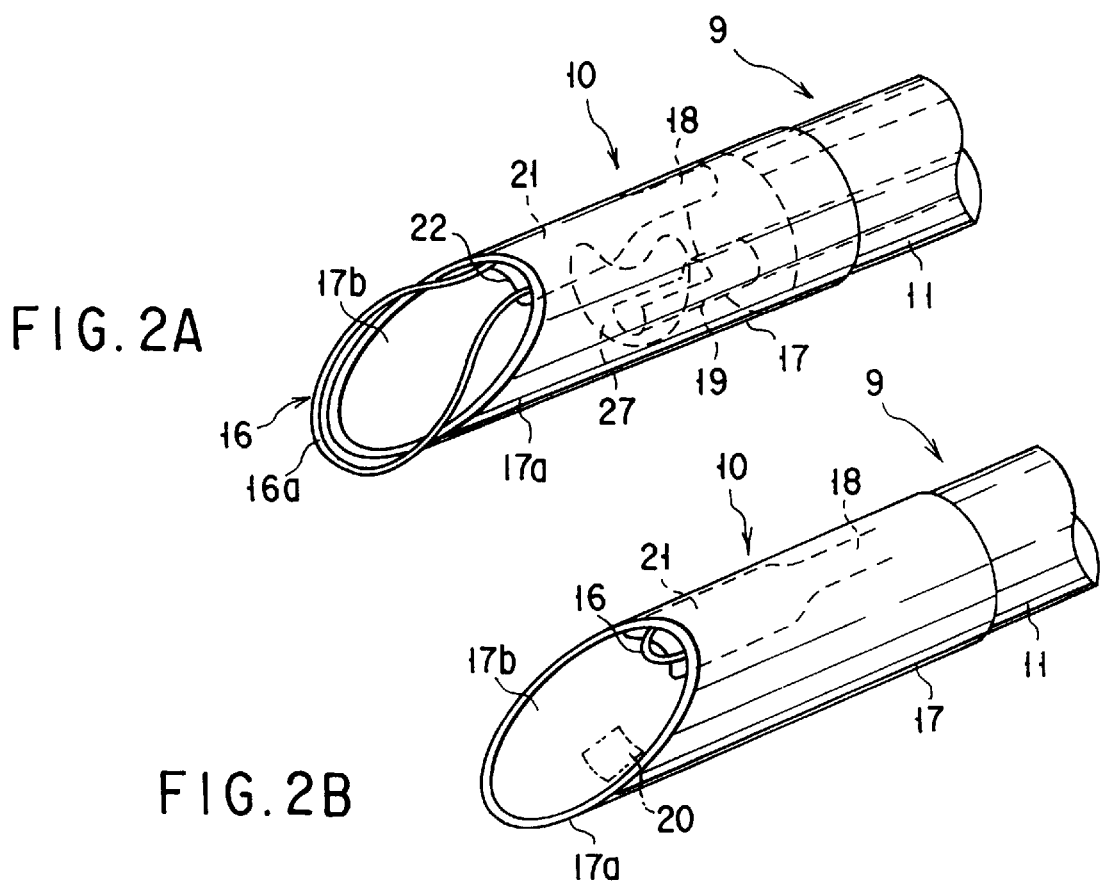
FIG. 2A
FIG. 2B
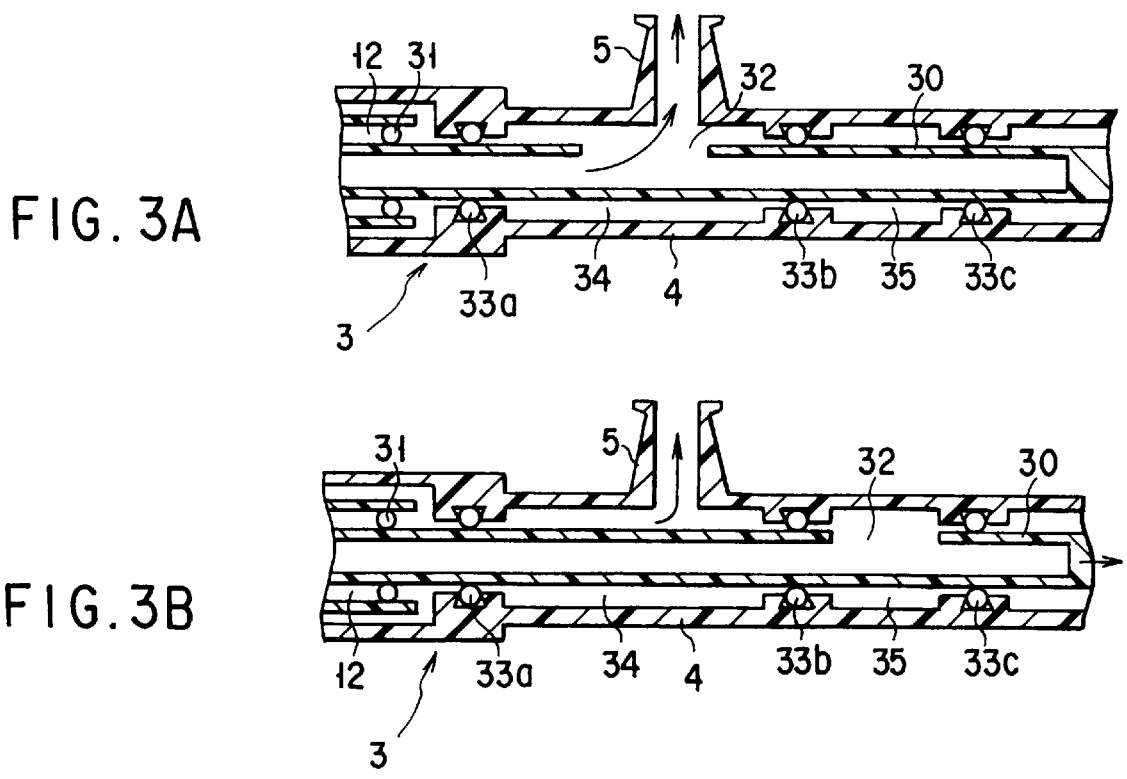
FIG. 3A
FIG. 3B

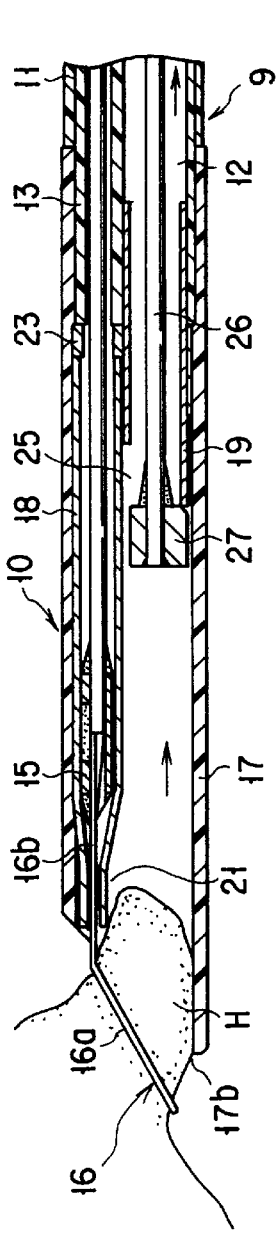
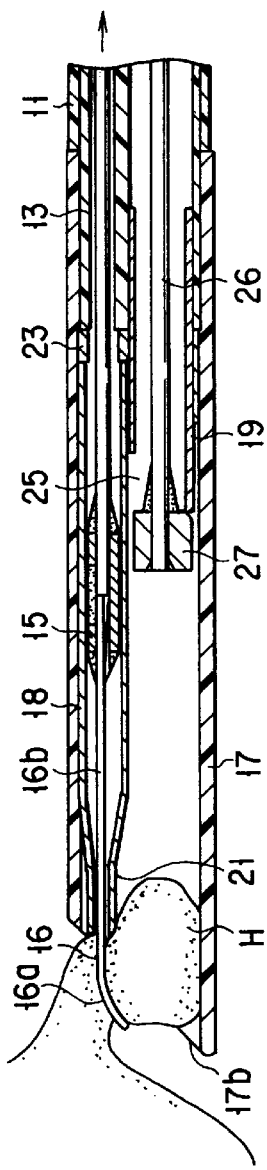
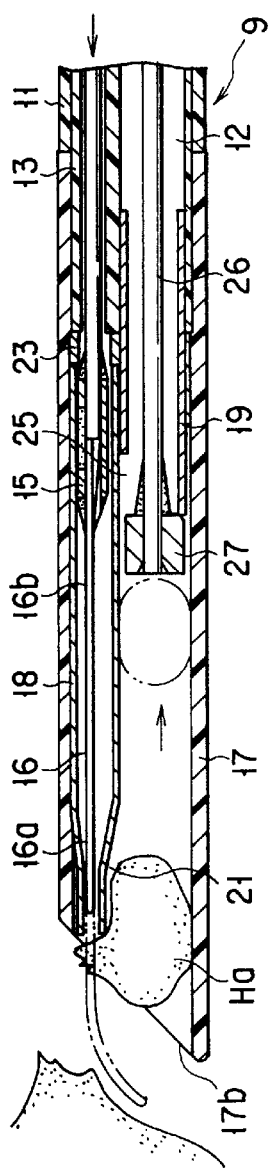
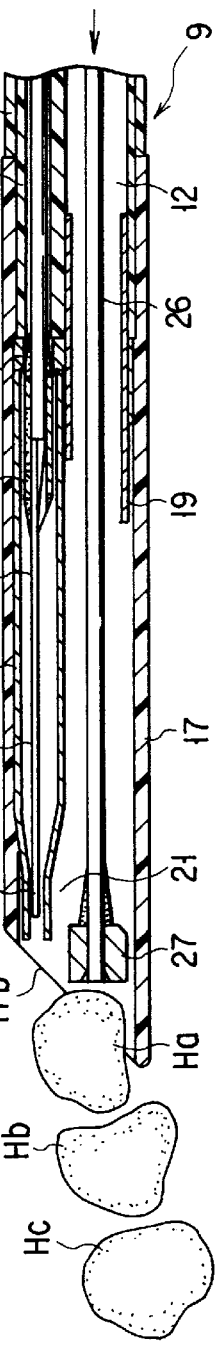
FIG. 4A
FIG. 4B
FIG. 4C
FIG. 4D

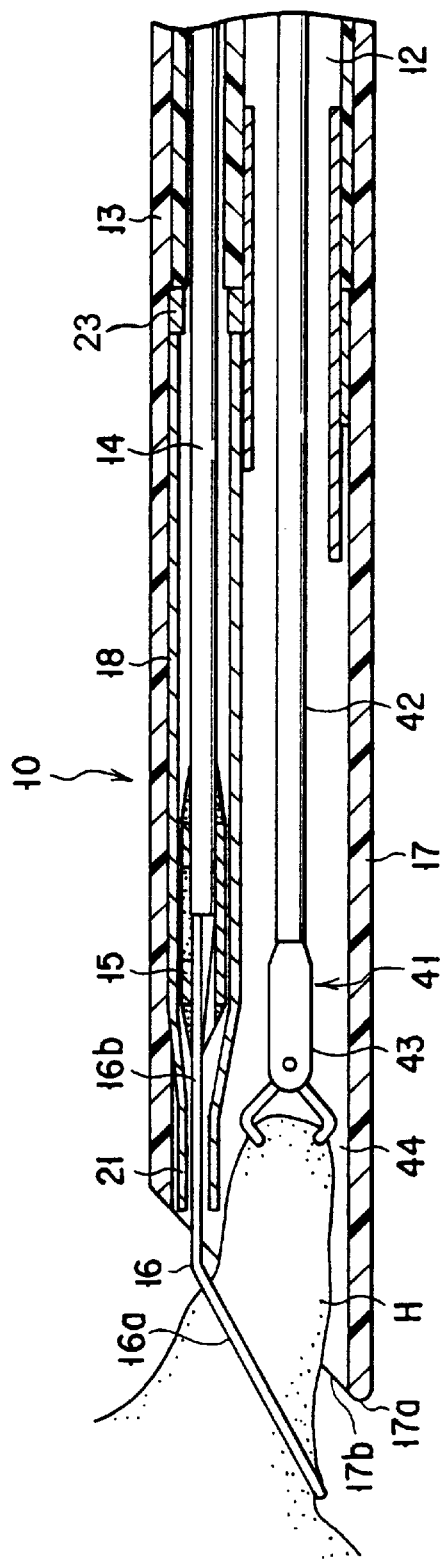
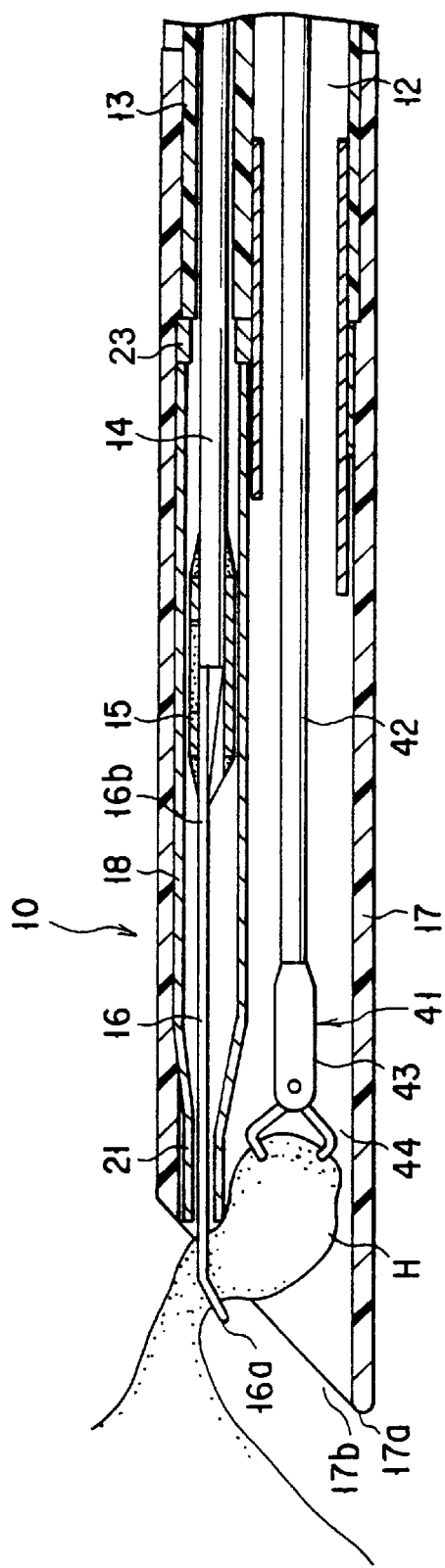
FIG. 5A
FIG. 5B

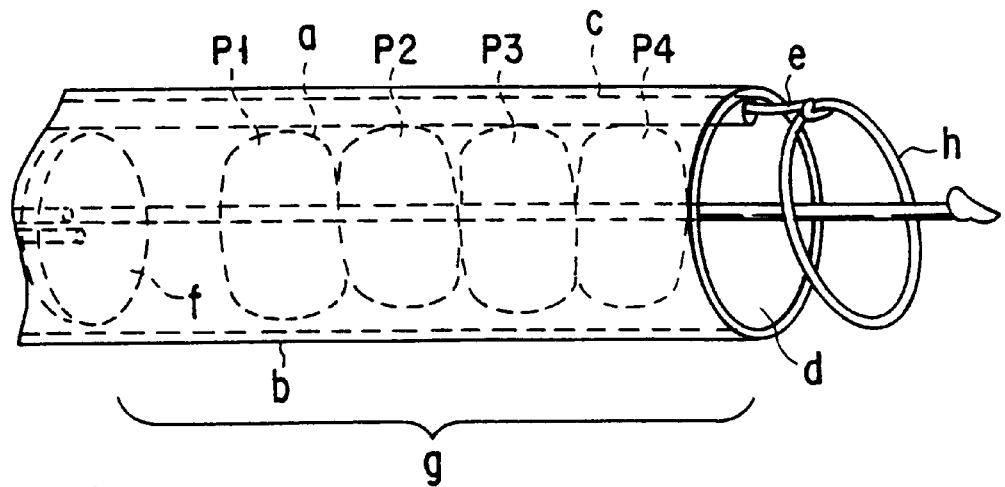
FIG. 13A
PRIOR ART
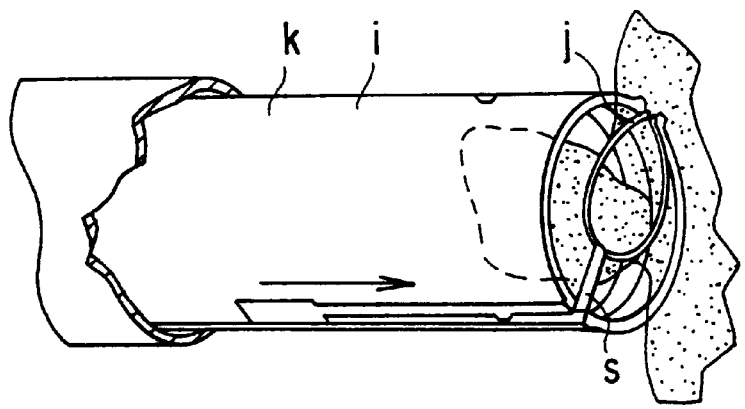
FIG. 13B
PRIOR ART
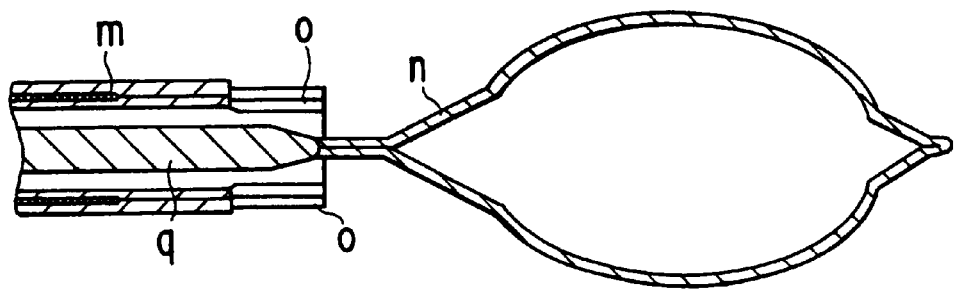
PRIOR ART  FIG. 13C

MEDICAL INSTRUMENT FOR USE IN COMBINATION WITH AN ENDOSCOPE

BACKGROUND OF THE INVENTION

This invention relates to a medical instrument which is designed to be inserted into a patient's body through the instrument guiding channel of an endoscope, already inserted into the patient's body, for continuously cutting living tissue and collecting a plurality of living tissue samples.

International Publication PCT WO95/08291, for example, discloses a medical instrument for sampling living tissue. FIG. 13A shows an essential part of a medical instrument (a) described in the publication. The medical instrument (a) has a flexible sheath (b) which can be inserted into an endoscope. The sheath (b) has an opening (d) at its distal end. A small-diameter inner tube (c) is inserted in the sheath (b). The inner tube (c) is fixed on the inner peripheral surface of the sheath (b).

An operational wire (e) is inserted in the inner tube (c). A looped cutting wire (h) is connected to an end of the operational wire (e). The cutting wire (h) can be protruded to the outside of the opening (d) of the flexible sheath (b) by operating the operational wire (e).

When the operational wire (e) has been pulled to the hand side, the cutting wire (h) is retreated into the flexible sheath (b) and the loop of the wire (h) is contracted.

When the operational wire (e) has been pushed, the cutting wire (h) is protruded to the outside of the sheath (b) through the opening (d). At this time, the loop of the cutting wire (h) expands due to its elastic force such that it crosses the opening (d). A retractor (f) is provided in the flexible sheath (b) for pushing and moving an excised tissue piece (p).

When using the medical instrument (a), it is inserted into the forceps channel of the endoscope. Then, the operational wire (e) is pushed to protrude the cutting wire (h) to the outside of the sheath (b) and expand it. In this state, living tissue is inserted into the sheath (b) through the opening (d) using the cutting wire (h).

After that, the operational wire (e) is pulled to the hand side, thereby pulling the cutting wire (h) into the flexible sheath (b). At this time, the loop diameter of the cutting wire (h) is gradually reduced while it is pulled into the flexible sheath (b). The living tissue already inserted in the sheath (b) is cut by the tightening force of the gradually diameter-reduced wire (h). The excised tissue piece (p) is contained in a tissue storing space (g) defined in the sheath (b).

This cutting operation is repeated a necessary number of times, and a plurality of excised tissue pieces p1, p2, p3 and p4 are sequentially stored in the tissue storing space (g). Thereafter, the medical instrument (a) is removed from the endoscope, and the retractor (f) is protruded to the outside of the sheath through the opening (d), thereby pushing the excised tissue pieces p1, p2, p3 and p4 out of the tissue storing space (g). Thus, the tissue pieces are collected.

European Patent EP 0761170 discloses a medical instrument of another structure. As is shown in FIG. 13B, it discloses a medical instrument (k) which has an outer cylinder (i), and a looped cutting wire (j) which can expand at an end of the outer cylinder (i). In this case, a living tissue piece is excised by pulling the cutting wire (j) from the end of the outer cylinder (j) into it.

Moreover, Japanese Patent Application No. 8-310664 (this document was published on Jun. 12, 1998 (KOKAI publication No. 10-146345) and had not yet been published when the present application was filed) discloses a medical instrument for endoscopes, which excises living tissue through an endoscope when a high frequency current is flown. In this case, as shown in FIG. 13C, an operational wire (q) is axially movably provided in a flexible sheath (m). A substantially looped cutting wire (n) is mounted at an end of the operational wire (q) such that it can protrude out of and retreat into the sheath (m). When a high frequency current is flown into the cutting wire (n) via the operational wire (q), it can excise living tissue.

Further, in this instrument, the sheath (m) has a slotted end portion (o). The loop of the cutting wire (n) is engaged with the slotted portion (o) when the wire (n) is pulled into the sheath (m). Where the loop of the cutting wire (n) is engaged with the slotted portion (o) of the sheath (m), the direction of the high frequency cutting wire (n) can be changed by rotating the wire (n) together with the sheath (m) when axially rotating the sheath (m).

When, in the case of the medical instrument disclosed in PCT WO95/08291, the cutting wire (h) has been pulled out of the flexible sheath (b) and has expanded due to its own elastic force, the expanded section of the wire (h) must be situated at the opening (d) of the sheath in order to excise tissue in good condition by the wire (h).

Since, however, the cutting wire (h) inserted in the sheath (b) is a relatively slender flexible wire, it may not sufficiently follow the rotation of the sheath (b). Accordingly, where the sheath (b) can easily rotate about its axis as in the operation of inserting the medical instrument (a) into the endoscope, it is highly possible that the cutting wire (h) inserted in the sheath (b) will not follow the axial rotation of the sheath (b). In this case, it is possible that the expanded section (h) of the cutting wire (h) will be displaced from the opening (d) of the flexible sheath (b) when the medical instrument (a) protrudes from the tip of the endoscope, thereby disabling collection of tissue.

Moreover, to correct the displacement of the expanded section of the cutting wire (h) from the opening (d) of the sheath (b), it is necessary to rotate the expanded section relative to the opening (d). Thus, handling of the medical instrument (a) is too much trouble.

Furthermore, European Patent EP 0761170 discloses means for limiting the direction of expansion of the cutting wire (j) by providing strap (s) at an end of the wire (j) and fixing one end of strap (s) to the outer peripheral surface of the outer cylinder (i).

In this case, however, fixing the strap (s) on the outer peripheral surface of the outer cylinder (i) inevitably complicates the structure of the medical instrument (k) and increases the outer diameter of the entire insertion section of the instrument (k). Accordingly, it is difficult to reduce the outer diameter of the entire insertion section to an extent which enables insertion of the insertion section of the instrument (k) into the forceps channel of the endoscope.

In addition, the strap (s) of the cutting wire (j) limit the movement of the wire (j) toward the axis of the outer cylinder (i). Thus, the strap (s) not only reduce the degree of freedom of the movement of the wire (j), but also become obstacles when grasping tissue by the wire (j).

In the case of the structure described in Japanese Patent Application No. 8-310664, a rather sharp edge portion may be formed at the slotted portion (o) of the sheath (m) with which the cutting wire (n) is engaged. This sharp edge portion may damage the wall surface of the forceps channel of the endoscope while the medical instrument is inserted into it, or may injure a mucous membrane in a cavity of the body.

BRIEF SUMMARY OF THE INVENTION

The invention has been developed in light of the above-described matters, and is aimed at providing a medical instrument for use in combination with an endoscope, which has a simple structure and can reliably excise tissue, with a predetermined relationship maintained between the expansion direction of a cutting wire and the direction of an open end of an outer sheath, and without damaging the wall of a forceps channel or injuring a mucous membrane in a cavity of the body.

To attain the aim, there is provided a medical instrument for use in combination with an endoscope, comprising:

a long, slender flexible sheath to be inserted into a patient's body through a channel of the endoscope;

operation means inserted in the sheath such that it is axially movable;

a looped cutting wire connected to a distal end of the operation means; and an operation section provided at a proximal end side of the flexible sheath for pushing and pulling the operation means to thereby protrude the cutting wire to the outside of the sheath and retreat the cutting wire into the sheath through a distal end of the sheath, wherein:

the cutting wire is elastically deformed in a direction in which its loop contracts, when it is retreated into the sheath, and deformed in a direction in which its loop expands, when it is protruded to the outside of the sheath;

the cutting wire cuts part of living tissue of the patient's body while it is pulled into the sheath after it is protruded to the outside of the sheath, thereby storing a cut and sampled piece in the sheath; and the sheath has, at its distal end, flat loop expansion direction regulating means for regulating the loop expansion direction of the cutting wire.

As described above, the cutting wire is guided by the flexible sheath, and engaged, at the distal end of the sheath, with those inner surfaces of the flat section of the flat loop-expansion-direction regulating means, which are situated in a direction of the major diameter of the flat section. By virtue of this structure, rotation of the cutting wire relative to the flexible sheath, which will occur when the loop of the cutting wire is protruded to the outside of the sheath, is prevented to thereby regulate the expansion direction of the loop of the cutting wire so that the wire can be always protruded in a predetermined direction. Therefore, the cutting wire is developed at the flat opening, which enables rotation of the cutting wire in accordance with the rotation of the sheath, i.e. enables positioning of the wire in a direction in which the wire can easily grasp tissue. Further, when sampling living tissue, the instrument is inserted into the patient's body through the forceps channel of the endoscope, thereby sucking target tissue into the expanded section of the cutting wire. The cutting wire is then axially moved to tightly hold and cut the target tissue. After that, the instrument is removed from the forceps channel of the endoscope.

The invention employs, at the distal end of the flexible sheath, the flat loop-expansion-direction regulating means for regulating the loop expansion direction of the cutting wire. This means that the positional relationship between the expansion direction of the cutting wire and the outside sheath can be kept constant with a simple structure, whereby living tissue can be sampled in a reliable manner without greatly damaging the wall of the forceps channel or a mucous membrane of the patient's body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1A is a schematic perspective view, showing the entire structure of a medical instrument according to a first embodiment of the invention, which is designed for use in combination with an endoscope;

FIG. 1B is a longitudinal sectional view, showing a distal-end of an insertion section incorporated in the medical instrument of the first embodiment;

FIG. 1C is a front view taken when viewing FIG. 1B in a direction indicated by arrow A;

FIG. 1D is a sectional view take along lines ID—ID of FIG. 1B;

FIG. 2A is a perspective view of an essential part of the medical instrument of the first embodiment, showing a state in which a snare provided at the distal end of an insertion section of the instrument is protruded to the outside of a distal end cover;

FIG. 2B is a perspective view an essential part of the medical instrument of the first embodiment, showing a state in which the snare is retreated in the distal end cover;

FIG. 3A is a longitudinal sectional view of an essential part of the medical instrument of the first embodiment, showing a suction state of an inner tube incorporated in the instrument;

FIG. 3B is a longitudinal sectional view of an essential part of the medical instrument of the first embodiment, showing a suction interrupted state of the inner tube incorporated in the instrument;

FIG. 4A is a longitudinal sectional view of an essential part of the medical instrument of the first embodiment, showing a state in which a living tissue is inserted in the loop of the snare during tissue sampling;

FIG. 4B is a longitudinal sectional view of an essential part of the medical instrument of the first embodiment, showing a state in which the living tissue is pulled into the distal end cover;

FIG. 4C is a longitudinal sectional view of an essential part of the medical instrument of the first embodiment, showing a state in which the living tissue is cut and stored within the distal end cover;

FIG. 4D is a longitudinal sectional view of an essential part of the medical instrument of the first embodiment, showing a state in which pieces of the living tissue are pushed out of the instrument;

FIG. 5A is a perspective view of an essential part of a medical instrument according to a second embodiment, which is designed for use in combination with an endoscope, showing a state in which a snare is protruded to the outside of a distal end cover;

FIG. 5B is a perspective view of an essential part of the medical instrument of the second embodiment, showing a state in which the snare is retreated in the distal end cover;

FIG. 13A is a perspective view, showing an example of a conventional medical instrument for sampling a living tissue;

FIG. 13B is a perspective view, showing a state of use of another conventional medical instrument; and FIG. 13C is a longitudinal sectional view, showing a state of use of a yet another conventional medical instrument.

DETAILED DESCRIPTION OF THE INVENTION

Figure 6A:
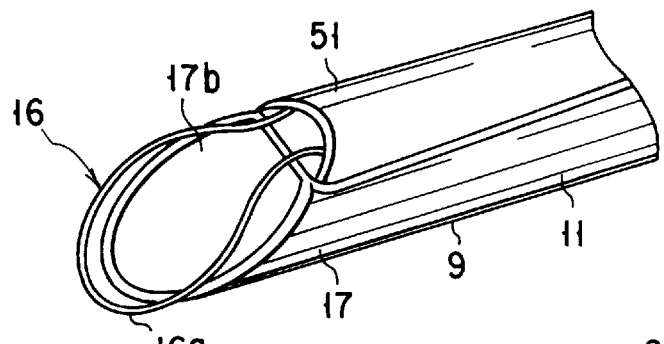
FIG. 6A is a perspective view, showing an essential part of a medical instrument according to a third embodiment, which is designed for use in combination with an endoscope.

Referring to FIGS. 1A–4D, a first embodiment of the invention will be described. FIG. 1A shows the entire structure of a medical instrument 1 according to the first embodiment, which is designed for use in combination with an endoscope. The medical instrument 1 comprises an insertion section 2 and an operation section 3. The insertion section 2 is long and slender and can be inserted into the forceps channel (instrument guiding channel) of an endoscope (not shown). The operation section 3 is secured to the proximal end of the insertion section 2.

The operation section 3 comprises a casing 4, which is formed of a substantially cylindrical member. The casing 4 has a suction port 5 outwardly projecting from an end thereof connected to the insertion section 2. An external suction means 6 having a connection tube 6a can be connected to the suction port 5 via the connection tube 6a. The suction means 6 may be an electrically driven pump, a manual pump, a rubber ball, a large syringe, etc.

A finger ring 7 is provided on the proximal end of the casing 4. An axially slidable slider 8 is mounted on the casing 4 between the suction port 5 and the finger ring 7.

The insertion section 2 comprises a thin, long flexible sheath 9 and a hard distal section 10 connected to the distal end of the sheath 9. The sheath 9 includes an outer tube 11 as shown in FIG. 1B. The outer tube 11 is made of a material which is flexible and has a sufficient strength against compression or tension. It is preferable that the outer tube 11 is a tightly wound coil, or a reinforced tube which is obtained by, for example, coating the inner and outer surfaces of a tube formed by weaving stainless steel wires, with a resin such as polyamide, tetrafluoroethylene, copolymer of tetrafluoroethylene and hexafluoropropylene, or polyethelene. Alternatively, the outer tube may be a reinforced tube which is obtained by attaching plural wires, over the entire length, to a tube formed of a resin material as above.

Further, as shown in FIG. 1D, a suction lumen 12 and a snare lumen 13 are provided in a cavity within the outer tube 11. The suction lumen 12 is airtightly provided in the cavity of the outer tube 11. The proximal end of the suction lumen 12 is airtightly connected to the suction port 5 of the operation section 3. The suction lumen 12 is formed of a material which can secure the airtightness of the lumen over the length thereof up to the hard distal section 10. The material is, for example, a resin such as tetrafluoroethylene, polyethylene, etc. or a metal having a high elasticity.

A snare wire (operating means) 14 is inserted in the snare lumen 13 such that it can axially move relative to the sheath 9. The distal end of the snare wire 14 is connected to the proximal end of a looped snare (cutting wire) 16 via a connection pipe 15.

As shown in FIG. 1B, the distal hard section 10 comprises a distal cover 17 fixed to the distal end of the outer tube 11, a snare pipe 18 fixed to the distal end of the snare lumen 13, and a suction pipe 19 fixed to the distal end of the suction lumen 12.

It is desirable that the distal cover 17 should be made of a flexible and transparent material, for example, a resin such as polyamide, tetrafluoroethylene, copolymer of tetrafluoroethylene and hexafluoropropylene, or polyethelene. However, the cover may be formed of a relatively hard resin such as polycarbonate.

An inclined portion 17a with an appropriate inclination angle θa to the axis of the medical instrument 1 is formed at the distal end of the cover 17. An elliptic opening 17b is formed in the inclined portion 17a.

An index 20 is secured to the outer peripheral surface of the cover 17 close to the distal end of the inclined portion 17a. The edge which defines the opening 17b is rounded so that it will not damage the forceps channel of the endoscope and the cavity of the patient's body. The distal end of the snare pipe 18 is secured to the rear end side of the inclined portion 17a of the cover 17.

The snare pipe 18 is a cylindrical guide means for guiding the snare 16. While being guided by the snare pipe 18, the snare 16 is movable along the axis of the flexible sheath 9 between a position shown in FIG. 2A in which the snare 16 projects to the outside of the distal cover 17 through the opening 17b, and a position shown in FIG. 2B in which the snare 16 is stored within the distal cover 17 through the opening 17b.

The snare pipe 18 may be formed of a relatively hard resin such as polysulfon, polyfenylsulfon, polycarbonate, etc. However, it is desirable that the pipe should be formed of a relatively flexible metal such as stainless steel or an Ni—Ti alloy with superelasticity.

The distal end of the snare pipe 18 is flattened and forms a flat section (loop expansion direction regulating means) 21. The flat section 21 regulates the direction of loop expansion of the snare 16. The flat section 21 has an edge 22 formed at the distal opening of the pipe is level with the opening 17b.

The outer diameter of the connection pipe 15 is slightly smaller than the inner diameter of the snare pipe 18. The forward movement of the connection pipe 15 is interrupted when the distal end of the pipe 15 contacts the proximal end of the flat section 21 within the snare pipe 18.

A stop ring 23 is secured to the proximal end of the snare pipe 18. The stop ring 23 has a hole 24 whose inner diameter is smaller than the outer diameter of the connection pipe 15. The rearward movement of the connection pipe 15 is interrupted when the proximal end of the pipe 15 contacts the front end of the stop ring 23.

The snare 16 has an expansible section 16a formed at its distal end, and a support section 16b formed in the rear of the expansible section 16a and consisting of a pair of linear wires. The expansible section 16a will show a substantially circular shape when it is expanded. Moreover, as shown in FIG. 1B, the expansible section 16a of the snare 16 is bent at a predetermined angle θb with respect to the rear support section 16b. The inclination angle θb is set smaller than the inclination angle θa of the distal cover 17 (θb<θa).

The area occupied by the loop section 16a when it is expanded is set sufficiently greater than the area of the opening 17b of the inclined portion 17a of the distal cover 17.

The snare 16 may be formed of stainless spring steel, a superelasticity alloy wire material such as an Ni—Ti alloy, or a resin such as polyamide, which are elastic sufficient to expand and contract and have a sufficient sharpness as knives. The outer diameter φ of the snare wire is set at, for example, about 0.1–0.2 mm to secure both sufficient tensile strength and sharpness necessary to cut living tissue. The minor diameter (opening width) of the edge 22 of the flat section 21 of the snare pipe 18 is set at a value at which almost no clearance is defined when the snare 16 passes through the opening.

A cutout 25 is formed in the outer peripheral surface of the distal end of the suction pipe 19. Further, a retractor 26 in the form of a wire is inserted in the suction pipe 19 such that it can protrude and retreat. A tissue stopper 27 is secured to the distal end of the retractor 26.

The size of the tissue stopper 27 is set at a value which enables its insertion into the distal cover 17 and also prevents movement of living tissue over the stopper 27 to the proximal end of the cover 17. Specifically, as shown in FIG. 1C, the area of the stopper 27 is set at about 60–80% of the area which is obtained by subtracting the cross section of the interior and wall of the snare pipe 18 from the cross section of the interior of the distal cover 17. Further, the shape of the stopper 27 is set at one which can be formed in the area obtained by subtracting the cross section of the snare pipe 18 from that of the cover 17.

A drawing section 28 for drawing the retractor 26 is protruded on the outer peripheral surface of the casing 4 of the operation section 3. The proximal end of the retractor 26 is extended to the outside of the instrument through the drawing section 28. An operation knob 29 for operating the retractor 26 is secured to the proximal end of the retractor 26.

The proximal end of the outer tube 11 is secured to the distal end of the operation section 3. The proximal end of the snare wire 14 is fixed to the slider 8 within the operation section 3. A movable pipe 30 is provided in the operation section 3 as shown in FIGS. 3A and 3B such that it can move along the axis of the medical instrument 1. The slider 8 is also secured to the movable pipe 30 in the operation section 3.

The distal end of the movable pipe 30 is airtightly and slidably connected to the proximal end of the suction lumen 12 by a sealing member 31. A suction hole 32 is formed in a proximal end portion of the movable pipe 30.

As illustrated in FIGS. 3A and 3B, three O-rings 33a, 33b and 33c are fitted in the casing 4 at appropriate intervals along the axis of the medical instrument 1.

The three O-rings 33a, 33b and 33c are fitted on the movable pipe 30. A first airtight chamber 34 is defined between the O-rings 33a and 33b, and a second airtight chamber 35 between the O-rings 33b and 33c. The first airtight chamber 34 communicates with the suction port 5 of the operation section 3.

The suction hole 32 of the movable pipe 30 is shifted between a first position shown in FIG. 3A and a second position shown in FIG. 3B as the slider 8 is moved back and forth in the axial direction of the operation section 3.

More specifically, when the slider 8 is in its fore position, the suction hole 32 is kept at the first position shown in FIG. 3A, where the hole 32 communicates with the first airtight chamber 34. At this time, the snare 16 is protruded to the outside of the snare pipe 18 as shown in FIG. 2A.

When the slider 8 is shifted to its rear position, the suction hole 32 is shifted to the second position shown in FIG. 3B, where the hole 32 communicates with the second airtight chamber 35. At this time, the snare 16 is stored within the distal cover 17 through the opening 17b as shown in FIG. 2B.

The operation of the above-described structure will now be described. When the medical instrument 1 according to the embodiment is used, the connection tube 6a of the external suction means 6 is previously connected to the suction port 5 of the operation section 3 and operated. In this state, the slider 8 is pulled to store the snare 16 into the snare pipe 18 as shown in FIG. 2B. At this time, the expansible section 16a of the snare 16 is kept elastically deformed between both the sides of the flat section 21 of the snare pipe 18.

Where the snare 16 is stored in the snare pipe 18, the suction hole 32 of the movable pipe 30 is shifted to the second position shown in FIG. 3B, where the hole 32 communicates with the second airtight chamber 35. Accordingly, in this state, negative pressure (i.e. a suction force created by the suction means 6) is prevented from being applied in the suction lumen 12.

Also, at that time, the proximal end of the connection pipe 15 in the distal hard section 10 is kept in contact with the front end of the stop ring 23. In this state, the insertion section 2 is inserted into the patient's body through the forceps channel of the endoscope.

To insert the insertion section 2, the endoscope or the medical instrument 1 is moved while observing the interior of the body through the endoscope, thereby guiding the distal hard section 10 of the insertion section 2 to a target mucous membrane H.

When the target mucous membrane H has been reached, the slider 8 is shifted to the distal end, thereby pushing the snare 16 out of the snare pipe 18 as shown in FIG. 2A. While the snare 16 is pushed, the expansible section 16a of the snare 16 moves in contact with longitudinal side surfaces of the edge 22 of the flat section 21 of the pipe 18. After the expansible section 16a passes through the flat section 21 of the pipe 18, it expands into a circular shape due to its own expanding force. More specifically, outside the snare pipe 18, the section 16a shows a circular shape just ahead of the opening 17b of the inclined portion 17a of the distal cover 17. The circular shape of the section 16a is similar in shape to and parallel in plane to the opening 17a as shown in FIG. 2A.

Further, when the section 16a of the snare 16 has expanded into a circular shape outside the snare pipe 18, the distal end of the connection pipe 15 in the distal hard section 10 contacts the proximal end of the flat section 21 of the snare pipe 18. At this time, the suction hole 32 of the movable pipe 30 is situated in the first position shown in FIG. 3A, where the hole 32 communicates with the first airtight chamber 34. Accordingly, negative pressure (a suction force created by the suction means 6) is applied in the suction lumen 12.

In this state, the opening 17b of the distal cover 17 is brought into contact with the target mucous membrane H, thereby sucking it into the opening 17b as shown in FIG. 4A.

Then, the slider 8 is pulled, thereby storing the section 16a of the snare 16 into the snare pipe 18 and tightly holding the membrane H, as is shown in FIG. 4B.

Subsequently, the slider 8 is further pulled, thereby cutting the membrane H sucked in the opening 17b of the distal cover 17, using the snare 16 and the edge 22 of the snare pipe 18, as is shown in FIG. 4C. The sampled piece Ha is located close to the opening 17b of the cover 17. Since at this time, as is shown in FIG. 3B the suction hole 32 of the movable pipe 30 is shifted into the second airtight chamber 35, the negative pressure applied in the suction lumen 12 is cut off.

Subsequently, the endoscope or the medical instrument 1 is operated to guide the distal hard section 10 to the next target mucous membrane H. After the next target membrane is reached, the distal end of the slider 8 is moved to protrude the snare 16 from the snare pipe 18. Since at this time, the suction hole 32 of the movable pipe 30 is shifted to the first airtight chamber 34, negative pressure is applied in the suction lumen 12. The negative pressure applied moves the first sampled piece Ha located in the cover 17 close to the opening 17b, to an inner portion of the cover 17 as indicated by the broken line in FIG. 4C. More precisely, the piece Ha is moved until it contacts the tissue stopper 27 of the retractor 26.

The above-described operation is repeated, thereby storing the first, the second, . . . and the n-th sampled pieces Ha, Hb, . . . in the distal cover 17 in this order. The second sampled piece Hb, for example, is stored in a portion of the cover 17 closer to the opening 17b than the first sampled piece Ha.

The maximum number of the pieces Ha, Hb, . . . which can be stored in the cover 17 is determined when the interior of the distal cover 17 is filled with such pieces and no negative pressure can be applied thereto.

After a desired number of pieces are sampled, the medical instrument 1 is removed from the forceps channel. Then, the suction means 6 is detached from the suction port 5, and the knob 29 is moved to the distal end side to protrude the tissue stopper 27 from the distal cover 17, thereby collecting the sampled pieces Ha, Hb, . . . in the order opposite to the storing order.

The above-described structure provides the following advantages: Since the embodiment employs the flat section 21 at that distal end of the snare pipe 18 through which the snare 16 is protruded and retreated, the direction of expansion of the section 16a of the snare 16 is kept constant and kept parallel to the opening 17b of the inclined portion 17a of the cover 17 when the section 16a is protruded to the outside of the snare pipe 18. Accordingly, it is not necessary to perform positioning for aligning the snare 16 with the opening 17b, which means that reliable sampling of tissue can be performed by a simple operation.

Moreover, the distal hard section 10 at the distal end of the sheath 9 is provided with both the opening of the flat section 21 of the snare pipe 18 for protruding the snare 16, and the opening 17b of the inclined portion 17a of the cover 17. By virtue of this structure, the medical instrument 1 can instantly cut living tissue having entered the distal cover 17, using the snare 16.

The snare pipe 18 provided at the distal end of the sheath 9 cooperates with the snare 16 to cut living tissue. Thus, sharply cut living tissue can be sampled.

Furthermore, the distal end of the cover 17 has the inclined portion 17a which inclines at the appropriate angle θa with respect to the axis of the medical instrument 1. This enables the formation of an opening 17b of a large area in the distal cover 17, and hence sampling of large tissue. Also, the inclined structure enables easier, smoother expansion/ storage operation of the snare 16 than the case where the opening 17b is perpendicular to the axis of the medical instrument 1.

Since the expansible section 16a of the snare 16 is formed oblique, the distance between itself and the inclined portion 17a, i.e. the opening 17b, of the cover 17 can be minimized, which facilitates reception of the living tissue into the opening 17b. This also enables easy and smooth expansion/ storage of the expansible section 16a of the snare 16.

Further, since the distal edge 22 of the flat section 21 of the snare pipe 18 is level with the distal opening 17b of the distal cover 17, living tissue received in the opening 17b can be reliably caught and cut.

Since living tissue can be kept sucked in the distal opening 17b of the cover 17 by negative pressure which is created by the suction means 6, it is not necessary to puncture the tissue with the opening 17b, and hence not necessary to form a very sharp opening 17b. This being so, tissue sampling can be performed without hurting the patient's body.

Since the distal cover 17 has a storage space for storing excised tissue pieces Ha, . . . , a plurality of living tissue pieces can be sampled without removing the medical instrument 1 from the endoscope.

In addition, since the distal cover 17 is made of a transparent material, storage of pieces Ha, Hb, . . . can be confirmed with the eyes through the endoscope, and hence sampling be performed without failure. Further, the tissue stopper 27 and the retractor 26 much facilitate the collection of plural sampled pieces.

The edge 22 of the flat section 21 of the snare pipe 18 cooperates with the snare 16 to cut tissue. Thus, a mucous membrane H can be cut sharply.

The outer diameter of the wire material of the snare 16 is set at about 0.1–0.2 mm, which enables mechanical cutting of the membrane H even when no high frequency current is flown into the snare 16.

Yet further, since the snare 16 is made of a superelastic material, the shape of the expanded snare 16 is not easily deformed even after storage of the snare 16 is repeated or holding/cutting of living tissue by the snare 16 is repeated. Thus, the medical instrument 1 is highly durable under repeated use.

FIGS. 5A and 5B show a second embodiment of the invention. This embodiment is obtained by altering the medical instrument 1 of the first embodiment (shown in FIGS. 1A–4D) as described below. In FIGS. 5A and 5B, similar structural elements to those in the first embodiment are denoted by corresponding reference numerals, and no explanations will be given thereof.

In the second embodiment, a grasping means 41 which can be protruded from and retreated into the distal cover 17 is provided in the suction lumen 12 of the outer tube 11, in place of the suction means 6.

The grasping means 41 includes an operation wire 42 which is slidable inserted in the suction lumen 12, a distal unit 43 connected to the distal end of the wire 42, a pair of openable grasping members 44 incorporated in the distal unit 43, and an opening/closing mechanism incorporated in the distal unit 43 for opening/closing the grasping members 44.

To protrude the grasping means 41 to the outside of the distal opening 17b of the distal cover 17 during use of the medical instrument 1 of the embodiment, the grasping means 41 is protruded through the expansible section 16a of the snare 16 to grasp a mucous membrane H. Then, the grasping means 41 is pulled to the proximal end of the instrument to thereby pull the membrane H into the distal cover 17 as shown in FIG. 5A.

After that, the slider 8 is pulled, thereby storing the expansible section 16a of the snare 16 into the snare pipe 18 to tightly hold the membrane H, as is shown in FIG. 5B.

The above-described structure provides the following advantages:

The second embodiment employs, in the suction lumen of the outer tube 11, the grasping means 41 which can be protruded from and retreated into the distal cover 17, in place of the suction means 6 provided at the proximal end side of the sheath 9 in the first embodiment. Accordingly, living tissue can be pulled into the distal cover 17 without using the suction means 6.

Further, since the grasping means 41 for grasping the target mucous membrane H makes it unnecessary to bring the distal opening 17b of the inclined portion 17a of the cover 17 into precise contact with the membrane H. This means that the degree of target shooting is enhanced.

FIG. 6A shows a third embodiment of the invention. This embodiment is obtained by altering the medical instrument 1 of the first embodiment (shown in FIGS. 1A–4D) as described below.

In this embodiment, an external snare pipe 51 for storing the snare 16 is provided on the outer peripheral surface of the sheath 9 of the insertion section 2. The distal end of the snare pipe 51 extends to the distal opening 17b of the distal cover 17. The other structural elements of the third embodiment are similar to those employed in the first embodiment, and hence no explanations will be given thereof.

Since in this structure, the snare pipe 51 is externally provided on the sheath 9 of the insertion section 2, the entire inner space of the distal cover 17 can be used as a sample storing space. Further, the instrument is free from, for example, the disadvantage that sampled pieces Ha, . . . stored in the cover 17 are caught and damaged by the snare pipe 51.

Figure 6B:
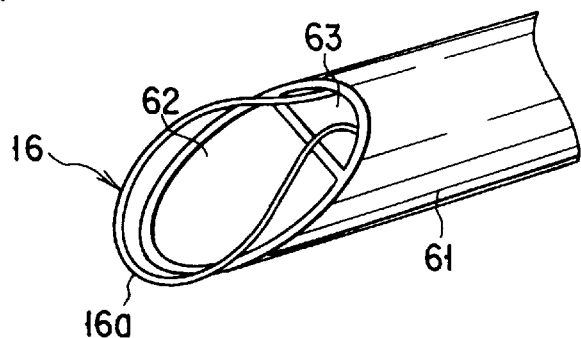
FIG. 6B is a perspective view, showing an essential part of a medical instrument according to a fourth embodiment, which is designed for use in combination with an endoscope.

FIG. 6B shows a fourth embodiment of the invention. This embodiment is obtained by altering the medical instrument 1 of the third embodiment (shown in FIG. 6A) as described below.

This embodiment employs a multi-lumen tube 61 which is obtained by integrally forming, as one body, the external snare pipe 51 and the sheath 9 of the insertion section 2. The multi-lumen tube 61 includes a large first lumen 62 corresponding to the sheath 9 of the insertion section 2 of the third embodiment, and a small second lumen 63 corresponding to the external snare pipe 51. The first lumen 62 is used to store sampled pieces, while the second lumen 63 is used to store the snare 16. The other structural elements are similar to those employed in the first embodiment, and hence no description will be given thereof.

As in the third embodiment, the instrument of the fourth embodiment is free from, for example, the disadvantage that sampled pieces Ha, . . . stored in the first lumen 61 are caught and damaged by the snare pipe 51. The instrument of the fourth embodiment is also advantageous in that the multi-lumen tube 61 obtained by integrally forming the external snare pipe 51 and the sheath 9 of the insertion section 2 in the third embodiment reduces the number of the entire component parts and hence facilitates the assemblage of the medical instrument.

Figure 7:
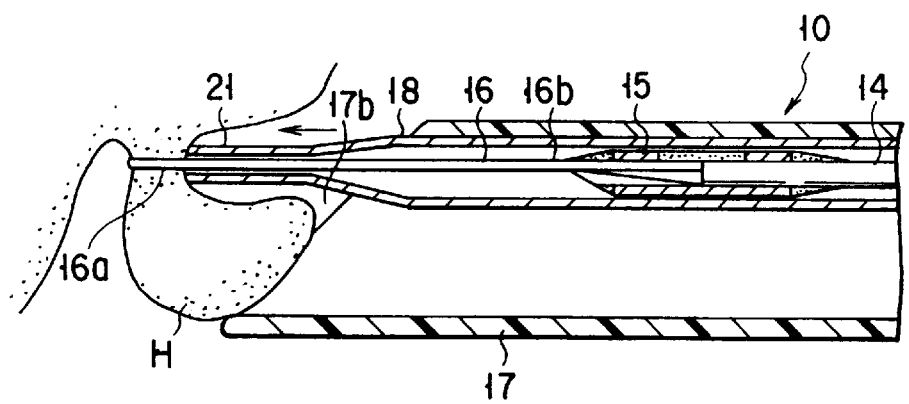
FIG. 7 is a perspective view, showing an essential part of a medical instrument according to a fifth embodiment, which is designed for use in combination with an endoscope.

FIG. 7 shows a fifth embodiment of the invention. This embodiment is obtained by altering the medical instrument 1 of the first embodiment (shown in FIGS. 1A–4D) as described below.

In this embodiment, the snare pipe 18 can be protruded to the outside of the distal cover 17 and retreated into the cover 17 through the opening 17b. The snare pipe 18 is supported by the inner peripheral surface of the cover 17 using an appropriate support member, such that it is slidable along the axis of the sheath 9, together with, for example, a snare lumen 13. The other structural elements in this embodiment are similar to those employed in the first embodiment, and hence will not be described.

When using the medical instrument 1 of the fifth embodiment, first, the snare 16 is protruded from the opening 17b of the distal cover 17 to suck a mucous membrane H into the expanded section 16a of the snare 16.

Subsequently, the snare pipe 18 is protruded out of the opening 17b of the cover 17 with the snare fixed, as is shown in FIG. 7. After that, the snare 16 is retreated into the snare pipe 18 to thereby tightly hold the membrane H.

Since in the above structure, the snare 16 does not move axially with respect to the opening 17b of the cover 17 when the membrane H is held after it is sucked into the expanded section 16a of the snare 16, there is no possibility of the membrane's slipping and escaping therefrom.

Figure 8:
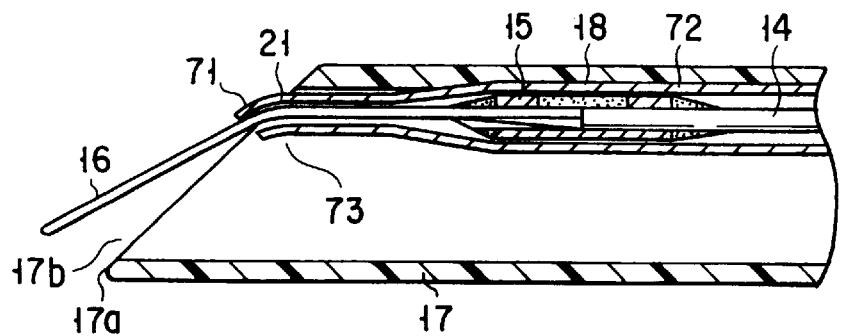
FIG. 8 is a perspective view, showing an essential part of a medical instrument according to a sixth embodiment, which is designed for use in combination with an endoscope.

FIG. 8 shows a sixth embodiment of the invention. This embodiment is obtained by altering the medical instrument 1 of the first embodiment (shown in FIGS. 1A–4D) as described below.

In this embodiment, the expansible section 16a of the snare 16 is not inclined with respect to a rear-side support section 16b of the snare 16 (the inclination angle θb=0), while a distal end section 71 of the snare pipe 18 has a bent section 73 which is inclined at a predetermined angle θc with respect to a rear-side section 72 of the pipe 18.

When the snare 16 has been protruded from the snare pipe 18 during the use of the medical instrument 1, it is developed in accordance with the shape of the bent section 73, thereby forming a loop section 16a just ahead of the opening 17b of the distal cover 17.

Although in the above structure, the expansible section 16a of the snare 16 is not inclined with respect to the rear-side support section 16b, it can be arranged parallel in plane to the opening 17b of the distal cover 17. Therefore, the snare 16 is free from reaction of bending which will occur in the case where the section 16a is bent from the rear-side support section 16b. Accordingly, the snare 16 is free from non-plastic deformation.

Figure 9A:
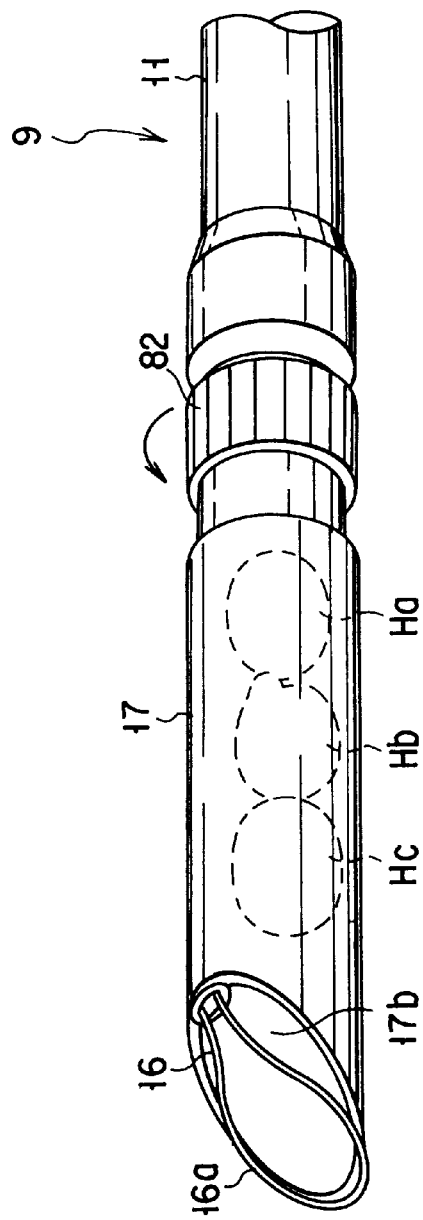
FIG. 9A is a perspective view of an essential part of a medical instrument, according to a seventh embodiment, for use in combination with an endoscope, showing a state in which a distal end cover is connected.
Figure 9B:
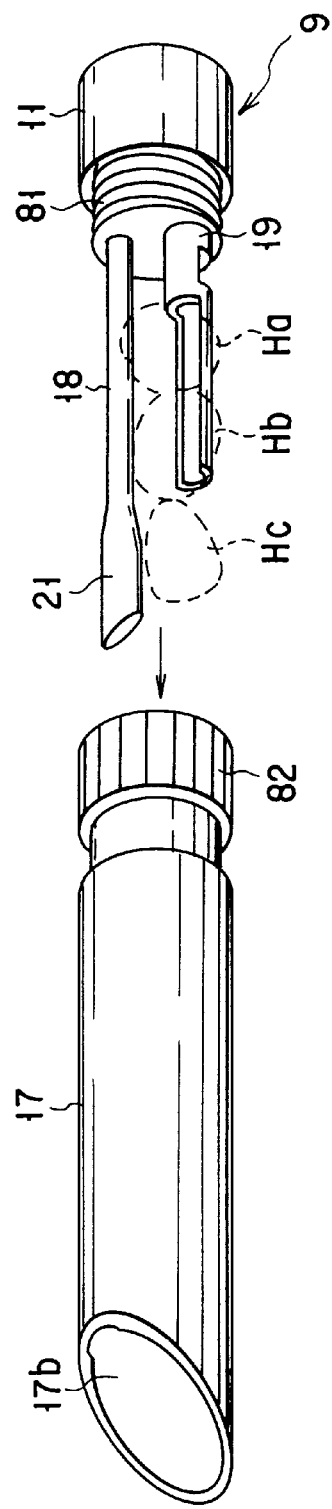
FIG. 9B is a perspective view of an essential part of the medical instrument of the seventh embodiment, showing a state in which the distal end cover is disconnected.

FIGS. 9A and 9B show a seventh embodiment of the invention. This embodiment is obtained by altering the medical instrument 1 of the first embodiment (shown in FIGS. 1A–4D) as described below.

In this embodiment, a male screw section 81 is provided at the distal end of the outer tube 11 of the sheath 9 as shown in FIG. 9B. Further, a sleeve 82, which is screwed onto the male screw section 81, is provided at the proximal end of the distal cover 17. Thus, the medical instrument 1 is constructed such that the cover 17 can be connected to the outer tube 11 of the sheath 9 by screwing the sleeve 82 onto the male screw section 81.

After the medical instrument 1 is removed from the forceps channel of the endoscope, the distal cover 17 can be pulled out of the distal end of the outer tube 11 by rotating the sleeve 82 and disengaging it from the male screw section 81. As a result, plural sampled pieces Ha, Hb, . . . stored in the distal cover 17 can be easily exposed to the outside of the instrument and collected.

Since in the above structure, plural sampled pieces Ha, Hb, . . . stored in the distal cover 17 can be collected without using the axially movable retractor 26 and the tissue stopper 27, the piece collecting mechanism can be made simple in structure, and the collecting operation can be performed more easily.

Figure 10:
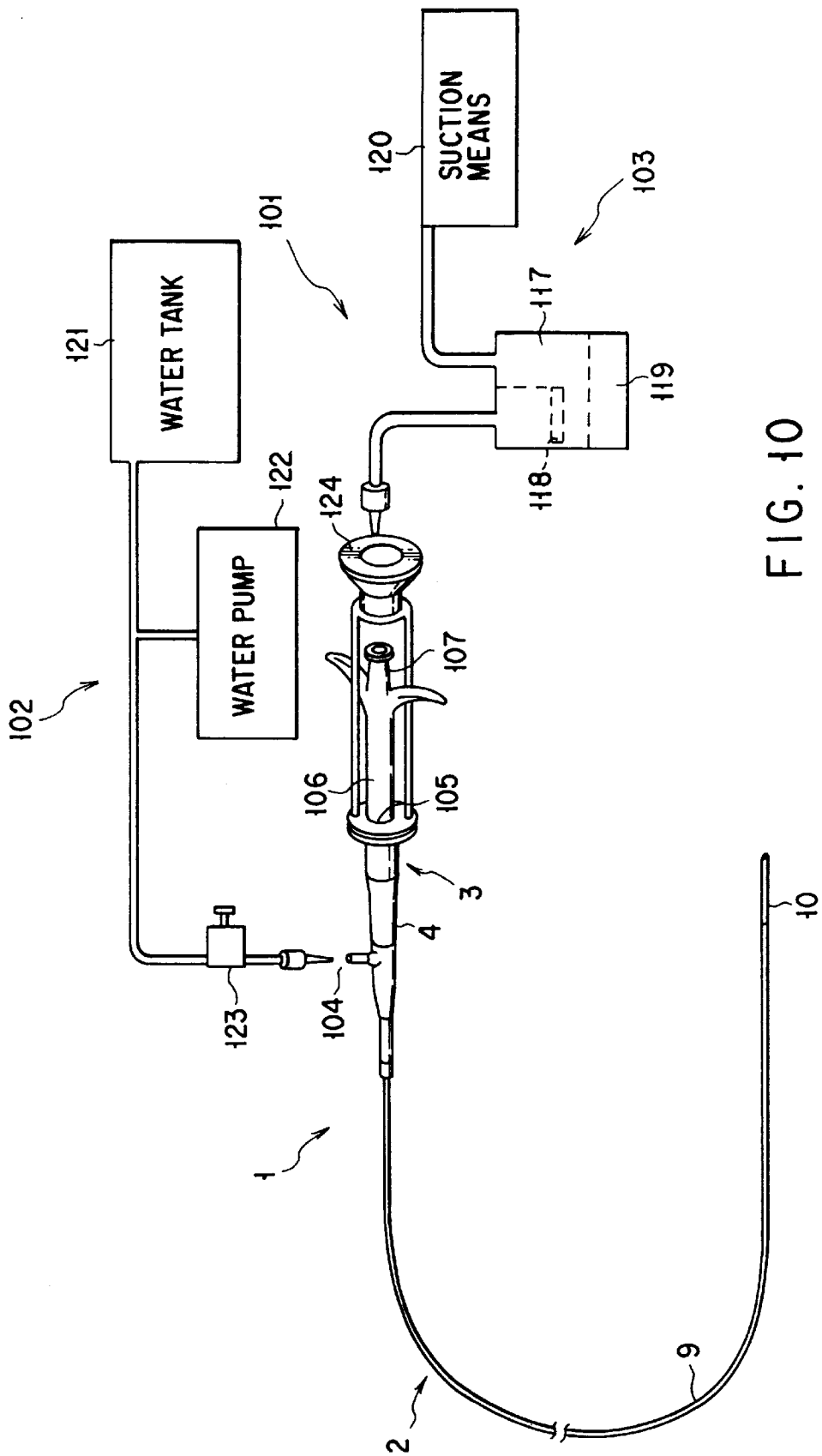
FIG. 10 is a schematic perspective view, showing the entire structure of a medical instrument according to an eighth embodiment of the invention, which is designed for use in combination with an endoscope.
Figure 11A:
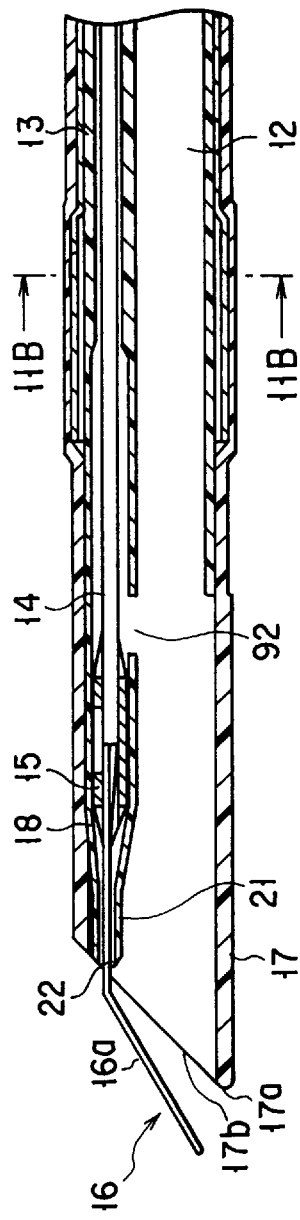
FIG. 11A is a longitudinal sectional view, showing a distal-end of an insertion section incorporated in the medical instrument of the eighth embodiment.
Figure 11B:
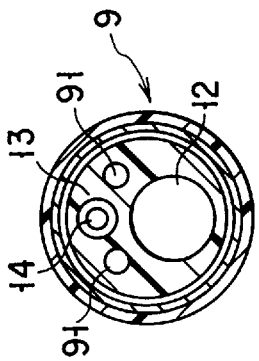
FIG. 11B is a view taken along lines 11B—11B of FIG. 11A.
Figure 11C:
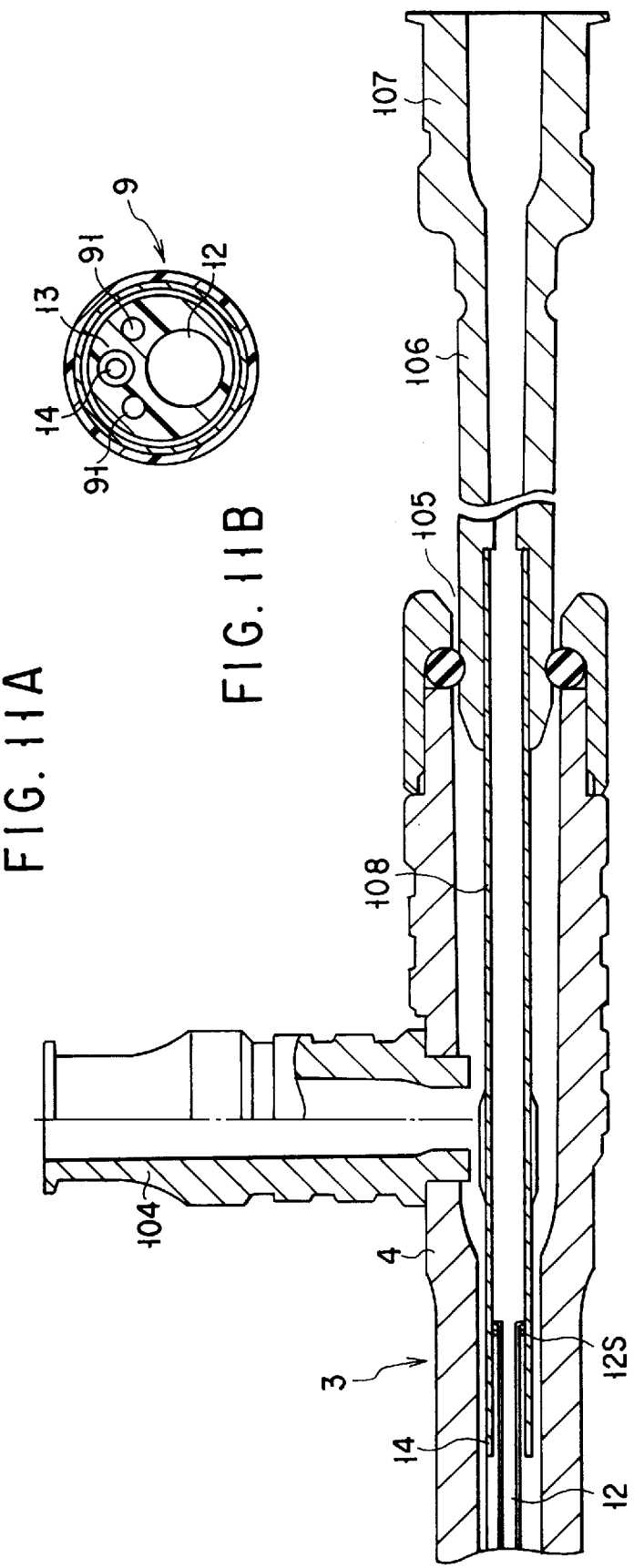
FIG. 11C is a longitudinal sectional view of an operation section incorporated in the instrument of the eighth embodiment.

FIGS. 10–11C show an eighth embodiment. This embodiment is obtained by altering the medical instrument 1 of the first embodiment (shown in FIGS. 1A–4D) as described below. FIG. 10 roughly shows the entire structure of the medical instrument 1 of the eighth embodiment. In this embodiment, similar elements to those in the first embodiment are denoted by corresponding reference numerals, and no description will be given thereof.

This embodiment employs a collecting system 101 for collecting sampled pieces Ha, Hb, . . . without removing the medical instrument 1 from the forceps channel of the endoscope. The collecting system 101 includes a water supply unit 102 and a sample collecting unit 103, which are to be coupled to the operation section 3 of the instrument 1.

A projecting water supply port 104 is provided on that distal end portion of the casing 4 of the operation section 3 which is close to the insertion section 2 of the instrument 1. Further, a rear end opening 105 is formed in the proximal end of the casing 4. A distal end portion of a substantial cylindrical slider 106 is axially movably inserted in the rear end opening 105. A collecting port 107 is provided in the rear end of the slider 106.

As is shown in FIGS. 11A–11C, the suction lumen 12 in the sheath 9 of the instrument 1 is airtightly connected to the distal end of the slider 106 with a seal member 12s interposed therebetween, and communicates with the collecting port 107 via the slider 106. The proximal end of the snare wire 14 is secured, in the operation section 3, to a connecting tube 108 at the collecting port 107 side, as is shown in FIG. 11C.

The snare lumen 13 is formed of an air-impermeable material and airtightly connected to the water supply port 104 of the operation section 3. Two water lumens 91 made of an air-impermeable material is provided in the sheath 9 as shown in FIG. 11B. The water supply lumens 91 has a distal end opening into the distal cover 17 and a proximal end airtightly connected to the water supply port 104 of the operation section 3.

The cross section of the inner space of the suction lumen 12 is set at 1.0 mm$^2$ or more. The sum of the cross section of the snare lumen 13 except for that of the snare wire 14, and the cross section of the water supply lumens 91 is set at 0.5 mm$^2$ or more.

The sheath 9 is formed of a flexible material which has a sufficient strength against compression and tension. For example, a reinforced tube is suitable for the sheath 9, which is obtained by coating the inner and outer surfaces of a tube formed by weaving stainless steel wires, with a resin such as polyamide, tetrafluoroethylene, copolymer of tetrafluoroethylene and hexafluoropropylene, or polyethelene. Moreover, the outer diameter of the sheath 9 is set at a value which permits its insertion into the forceps channel of the endoscope, i.e. about 2–4 mm. A communication hole 92 is formed in a distal end portion of the snare pipe 18, thereby causing the snare lumen 13 and the suction lumen 12 to communicate with each other. A sample trap 117 is provided in the sample collecting unit 103. A sample filter 118 is detachably provided in the sample trap 117, and a water reservoir tank 119 is provided below the trap 117. The collecting port 107 of the casing 4 of the operation section is connected to a suction means 120 via the sample trap 117.

The water supply unit 102 includes a water supply tank 121 and a water supply pump 122. The water supply tank 121 is connected to the water supply port 104 of the casing 4. The water supply pump 122 is interposed between the water supply port 104 and the water supply tank 121, and is operable when necessary. A stop valve 123 is provided between the water supply pump 122 and the water supply port 104. A finger position section 124 is secured to a portion of the operation section 3 close to the collecting port 107.

The operation of the above-described structure will be described. When using the medical instrument 1 of this embodiment, the water supply unit 102 is beforehand connected to the water supply port 104 of the operation section 3, and the sample collecting unit 103 is connected to the collecting port 107. The suction means 120 is started to be driven before using the instrument.

After that, the slider 106 is pulled to store the snare 16 into the snare pipe 18. Keeping this state, the insertion section 2 is inserted into the patient's body through the forceps channel of the endoscope.

While observing the inserted state of the insertion section 2 through the endoscope, the endoscope or the medical instrument 1 is moved to guide the distal hard section 10 of the insertion section 2 to a target mucous membrane H. When the section 10 has reached the target mucous membrane H, the slider 106 is shifted to the distal end side, thereby pushing the snare 16 out of the snare pipe 18 and permitting it to expand. In this state, the opening 17b of the distal cover 17 is brought into contact with the target mucous membrane H, thereby sucking it into the opening 17b.

Thereafter, the slider 106 is pulled, thereby storing the section 16a of the snare 16 into the snare pipe 18 and tightly holding the membrane H (shown in FIG. 4B). Subsequently, the slider 106 is further pulled, thereby cutting the membrane H sucked in the opening 17b of the distal cover 17, using the snare 16 and the edge 22 of the snare pipe 18. The sampled piece Ha is located close to the opening 17b of the cover 17.

When in this state, the stop valve 123 has been opened, negative pressure is applied to the snare lumen 13 and the water supply port 104 via the water supply lumens 91 and the communication hole 92, with the result that water in the water supply tank 121 is sucked into the distal cover 17.

At this time, the sampled piece Ha is mixed with the sucked water and air flown through the opening 17b of the distal cover 17, and is flown into the suction lumen 12 and then into the collecting port 107.

If the sampled piece Ha blocks the suction lumen 12, the water supply pump 122 is driven to increase the amount of water supplied to the suction lumen 12 via the water supply lumens 91 and the snare lumen 13, thereby releasing the blocking.

Moreover, the sampled piece Ha having passed the collecting port 107 is caught by the sample filter 118, and at the same time, the sucked water is stored in the reservoir tank 119. After that, the sample filter 118 is detached from the sample trap 117, thereby permitting collection of the piece Ha.

After collecting the sampled piece Ha, the same operation as above is repeated to thereby collect a desired number of sample pieces, and then the medical instrument 1 is removed from the forceps channel.

The above-described structure has the following advantages:

A plurality of sampled pieces Ha, Hb, . . . can be collected immediately after they are sampled, before the instrument 1 is removed from the forceps channel. Further, since the pieces Ha, Hb, . . . are collected one by one, this instrument is free from the disadvantage that the sampled pieces are mixed and the sampling order of the pieces becomes ambiguous, or that the pieces become indiscriminable from each other.

FIGS. 12A–12D show a ninth embodiment. A high frequency snare 131 employed in this embodiment comprises a flexible sheath 132 and an operation section 133 connected to the proximal end of the sheath 132.

An operational wire 134 is provided in the sheath 132 such that it is movable back and forth. A snare 135 is secured to the distal end of the operational wire 134.

The operation section 133 includes a slider 136 connected to the distal end of the operational wire 134, and an operation main section 137 secured to the proximal end of the sheath 132. The slider 136 has a connection terminal 138 electrically connected to the operational wire 134. The connection terminal 138 can be connected to the connector of a high frequency power supply cord (not shown).

Figure 12A:
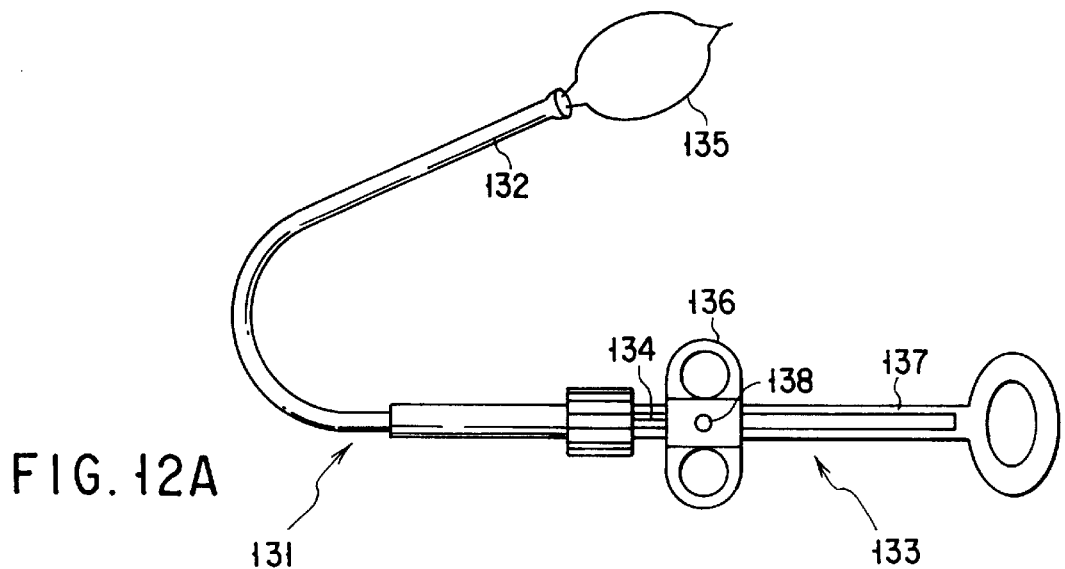
FIG. 12A is a schematic perspective view, showing the entire structure of a medical instrument according to a ninth embodiment of the invention, which is designed for use in combination with an endoscope.
Figure 12B:
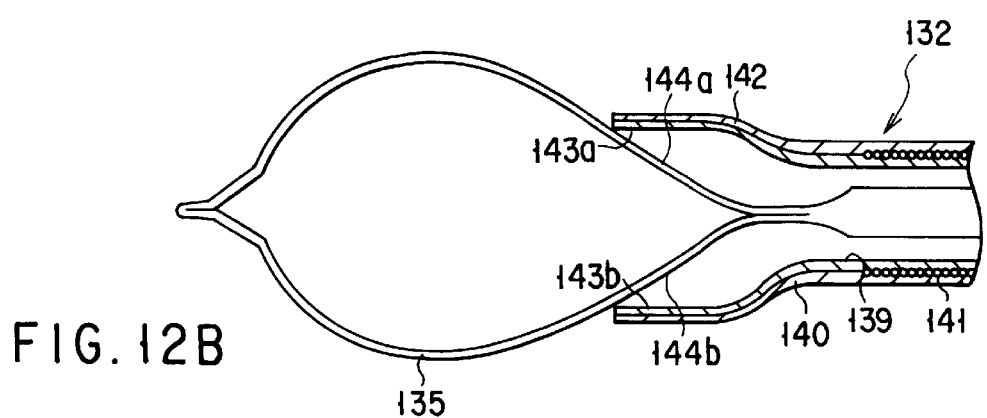
FIG. 12B is a longitudinal sectional view, showing a distal end section of the medical instrument of the ninth embodiment.

As shown in FIG. 12B, the sheath 132 is formed by adhering inner and outer resin tubes 139 and 140 to other, with a metallic reinforcing member 141 of a multi-start coil shape interposed therebetween. The reinforcing member 141 increases the torque transmission force of the flexible sheath 132.

The flexible sheath 132 has a flat section 142 at its distal end. The flat section 142 has opposite end surfaces 143a and 143b which can be engaged with proximal-end-side inclined sections 144a and 144b of a snare 135.

The operation of the above structure will be described. When a surface lesion 151 as shown in FIG. 12C has been found as a result of observation through the endoscope (not shown), a physiological salt solution is injected into the tissue with the surface lesion to thereby form a raised portion 153.

Subsequently, the high frequency snare 131 is inserted into the cavity through the forceps channel of the endoscope, thereby pushing the slider 136, and protruding the snare 135 from the distal end of the flexible sheath 132 to permit the snare to develop into a circular shape. If at this time, the resultant circular snare 135 is parallel in plane to a mucous membrane surface 152 with the surface lesion 151, it can easily catch the raised portion 153 therein.

Figure 12C:
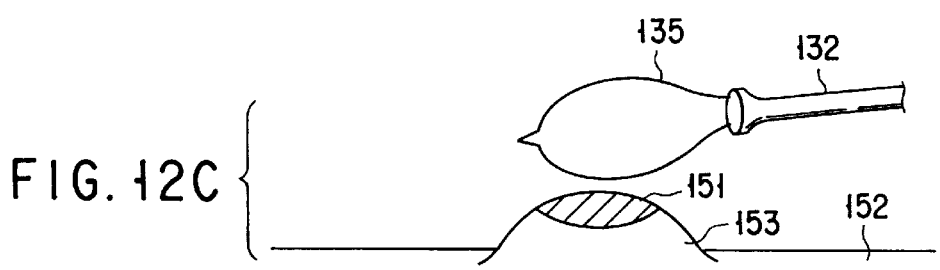
FIG. 12C is a perspective view, showing a state in which the loop of the snare incorporated in the medical instrument of the ninth embodiment is situated perpendicular to the surface of a mucous membrane.
Figure 12D:
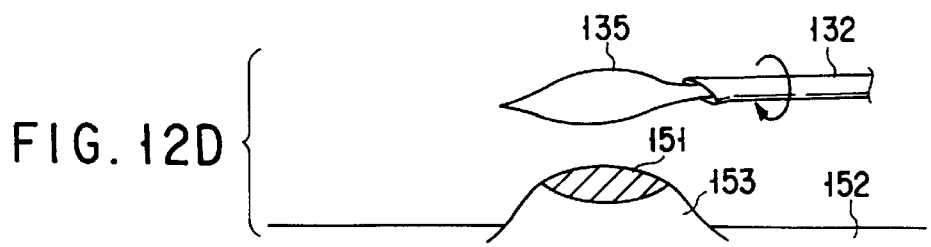
FIG. 12D is a perspective view, showing a state in which the medical instrument of the ninth embodiment is rotated until the loop of the snare is situated parallel to the mucous membrane.

If, on the other hand, the circular snare 135 is perpendicular to the mucous membrane surface 152 as shown in FIG. 12C, it cannot easily catch the raised portion 153 therein. In this case, the entire high frequency snare 131 is rotated by operating the proximal end of the instrument, thereby engaging the snare 135 with the distal flat section 142 of the sheath 132. As a result, the snare 135 rotates in accordance with the rotation of the sheath 132. The sheath 132 is rotated until the circular snare 135 becomes parallel in plane to the membrane surface 152 as shown in FIG. 12D. Then, the raised portion 153 is taken into the circular snare 135.

In this state, the slider 136 is pulled to pull the snare 135 into the flexible sheath 132, thereby contracting the snare 135 and tightly holding the root of the raised portion 153. Then, a high frequency current is flown into the snare 135 to thereby cut the raised portion 153.

Since in the above structure, the snare 135 can be reliably rotated by rotating the proximal-end of the flexible sheath 132, the loop of the snare 135 can be easily and reliably made parallel in plane to the membrane surface 152.

Naturally, the invention can be modified in various manners without departing from the scope thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. A medical instrument for use in combination with an endoscope, comprising:

an elongated flexible sheath to be inserted into a patient's body through a channel of the endoscope;

an operation unit inserted in the sheath such that it is axially movable;

a looped cutting wire connected to a distal end of the operation unit; and an operation section provided at a proximal end of the flexible sheath for pushing and pulling the operation unit to thereby protrude the cutting wire to the outside of the sheath and retreat the cutting wire into the sheath through a distal end of the sheath, wherein:

the cutting wire is elastically deformed in a direction in which its loop contracts, when it is retreated into the sheath, and deformed in a direction in which its loop expands, when it is protruded to the outside of the sheath;

the cutting wire cuts part of living tissue of the patient's body while it is pulled into the sheath after it is protruded to the outside of the sheath, thereby storing a cut and sampled piece in the sheath;

the sheath has, at its distal end, a flat loop expansion direction regulating section for regulating the loop expansion direction of the cutting wire; and the loop expansion direction regulating section has an opening of a flat cross section and is formed at the distal end of the sheath through which the cutting wire is protruded and retreated.

2. A medical instrument according to claim 1, wherein:

loop expansion direction regulating section comprises a flat-opening providing element which has said opening of a flat cross section, and a sharp edge for passing the cutting wire therethrough.

3. A medical instrument according to claim 1, wherein:

the loop expansion direction regulating section comprises a flat-opening providing element which includes said opening of a flat cross section.

4. A medical instrument according to claim 3, wherein:

the sheath includes a first opening for passing the cutting wire therethrough; and a second opening for receiving living tissue therethrough, and the flat-opening providing element is formed of the edge of the first opening.

5. A medical instrument according to claim 4, wherein:

the sheath has a sampled-piece storing section formed at the second opening for storing the sampled piece of the living tissue.

6. A medical instrument according to claim 5, wherein:

the sampled-piece storing section has a transparent portion.

7. A medical instrument according to claim 5, wherein:

the sheath has a pushing/pulling wire slidably inserted therein over the entire length of the sheath; and the pushing/pulling wire has a sampled-piece receiver secured to a distal end thereof for preventing the sampled piece of the living tissue from shifting to the proximal end of the sheath.

8. A medical instrument according to claim 5, wherein:

the sampled-piece storing section is detachably attached to the distal end of the sheath.

9. A medical instrument according to claim 3, wherein:

the sheath has, at the distal end thereof, a cutting pipe in which the cutting wire is inserted; and the flat-opening providing element comprises a distal end opening of the cutting pipe.

10. A medical instrument according to claim 9, wherein:
the cutting pipe is movable along the axis of the sheath.

11. A medical instrument according to claim 9, wherein;
the cutting pipe has a distal end which is secured on the same plane as the distal end of the sheath.

12. A medical instrument according to claim 9, wherein:
the sheath has, at the distal end thereof, an inclined portion which inclines with respect to the axis of the medical instrument; and the cutting pipe has, at its distal end, an inclined portion which is inclined in accordance with the inclined portion of the sheath.

13. A medical instrument according to claim 9, wherein:
the distal end opening of the cutting pipe has a sharp edge.

14. A medical instrument according to claim 3, wherein:
the sheath has, at the distal end thereof, an inclined portion which inclines with respect to the axis of the medical instrument; and the flat-opening providing element is located at a rear end of the inclined portion.

15. A medical instrument according to claim 14, wherein;
the flat-opening providing element has an inclined portion which is inclined in accordance with the inclined portion of the sheath.

16. A medical instrument according to claim 1, wherein:
the sheath has a sampled piece storing section formed therein for storing the sampled piece of the living tissue; and the sampled-piece storing section comprises a retractor provided at a rear end thereof which moves the stored piece to a distal end opening of the sheath.

17. A medical instrument according to claim 16, wherein:
the sheath has a suction pipe formed therein, the suction pipe having a proximal end connected to a suction source and a distal end communicating with the interior of the sampled-piece storing section; and the retractor is provided in the suction pipe.

18. A medical instrument according to claim 1, wherein:
the sheath has a suction pipe formed therein, the suction pipe having a proximal end connected to a suction source and a distal end communicating with a distal end opening of the sheath; and the suction pipe has a sampled-piece storing section formed between a proximal end of the sheath and the suction source for receiving the sampled piece of the living tissue.

19. A medical instrument according to claim 18, wherein:
the sheath has a water supply pipe formed therein, the water supply pipe having a distal end which communicates with the distal end opening of the sheath, and also a proximal end connected to a water supply.

20. A medical instrument according to claim 1, wherein:
cutting wire has an outer diameter of 0.1–0.2 mm.

21. A medical instrument according to claim 1, wherein:
the cutting wire is formed of a material having a super-elasticity.

22. A medical instrument according to claim 1, wherein:
the operation unit has, at a proximal end thereof, a connection section for receiving a high frequency current.

* * * * *